(12) United States Patent
Stefan et al.

(10) Patent No.: US 10,940,540 B2
(45) Date of Patent: Mar. 9, 2021

(54) SELF-SECURING COUPLING DEVICE AND METHOD

(71) Applicant: Karl Storz SE & Co. KG, Tuttlingen (DE)

(72) Inventors: Jochen Stefan, Tuttlingen (DE); Robin Merz, Tuttlingen (DE); Sven Grüner, Tuttlingen (DE)

(73) Assignee: Karl Storz SE & Co. KG, Tuttlingen (DE)

( * ) Notice: Subject to any disclaimer, the term of this patent is extended or adjusted under 35 U.S.C. 154(b) by 0 days.

(21) Appl. No.: 16/423,643

(22) Filed: May 28, 2019

(65) Prior Publication Data

US 2019/0358712 A1   Nov. 28, 2019

(30) Foreign Application Priority Data

May 28, 2018 (DE) .................... 10 2018 112 681.6

(51) Int. Cl.
*B23B 31/107* (2006.01)
*A61B 90/57* (2016.01)
(Continued)

(52) U.S. Cl.
CPC .......... *B23B 31/1071* (2013.01); *A61B 90/50* (2016.02); *A61B 90/57* (2016.02);
(Continued)

(58) Field of Classification Search
CPC . B23B 31/1071; B23B 31/1072; A61B 90/57; A61B 2090/0808; A61B 90/50; Y10T 279/17145; Y10T 279/17196
See application file for complete search history.

(56) References Cited

U.S. PATENT DOCUMENTS 1,119,276 A * 12/1914 Griffith et al. ...... B23B 31/1071
279/75
5,398,946 A *  3/1995 Quiring ............... B23B 31/1071
279/145
(Continued)

FOREIGN PATENT DOCUMENTS

DE         3401391 A1   7/1985
DE        19650447 A1   6/1998
(Continued)

OTHER PUBLICATIONS

European Search Report, Application No. EP 19 17 4292, completed: Oct. 16, 2019; dated Oct. 24, 2019, 9 pages.
(Continued)

*Primary Examiner* — Eric A. Gates
(74) *Attorney, Agent, or Firm* — Whitmyer IP Group LLC

(57) ABSTRACT

A coupling device and coupling method for the self-securing mechanical connection of two parts of a holding system for medical instruments, including a bolt element insertable into a bushing; wherein the bushing has a main body and, connected fixedly to the latter, a cone sleeve which tapers conically at its free end, wherein a cage sleeve acted upon by a spring and guiding clamping bodies is inserted axially movably into the cone sleeve and can be moved between an uncoupled position, a release position and a locking position. The clamping bodies in the locking position can be latched into a coupling groove of the bolt element by means of the spring force. The inclined coupling groove flank, at the front in the insertion direction, of the bolt element encloses an angle α with the longitudinal axis of the bolt element, and the cone inner face of the cone sleeve encloses an angle β with the central sleeve axis. The coupling device is characterized in that, for self-securing connection, the angle α is greater than the angle β such that clamping bodies partially or completely latched into the coupling groove can
(Continued)

be pressed into the locking position counter to the insertion direction by application of a tensile force to the bolt element.

17 Claims, 8 Drawing Sheets

(51) Int. Cl.
    *A61B 90/50*     (2016.01)
    *B23B 31/00*     (2006.01)
    *A61B 90/00*     (2016.01)
    *A61B 17/00*     (2006.01)

(52) U.S. Cl.
    CPC ........ *B23B 31/003* (2013.01); *B23B 31/1072* (2013.01); *A61B 2017/00477* (2013.01); *A61B 2090/0808* (2016.02); *Y10T 279/17145* (2015.01); *Y10T 279/3481* (2015.01)

(56) References Cited

U.S. PATENT DOCUMENTS

| | | | |
|---|---|---|---|
| 6,722,667 B2 * | 4/2004 | Cantlon | B23B 31/06 |
| | | | 279/155 |
| 6,818,005 B2 * | 11/2004 | Kupferschmid | A61B 17/29 |
| | | | 279/30 |
| 7,011,661 B2 * | 3/2006 | Riedel | A61B 17/162 |
| | | | 606/170 |
| 7,086,313 B2 * | 8/2006 | Cantlon | B25B 23/0035 |
| | | | 279/22 |
| 7,740,249 B1 * | 6/2010 | Gao | B23B 31/1071 |
| | | | 279/75 |
| 7,810,817 B1 * | 10/2010 | Gao | B23B 31/1071 |
| | | | 279/75 |
| 8,844,942 B1 * | 9/2014 | Landowski | B23B 31/1071 |
| | | | 279/75 |
| 8,882,113 B2 * | 11/2014 | Porter | B25B 23/0035 |
| | | | 279/75 |
| 9,414,848 B2 * | 8/2016 | Edwards | A61B 17/1633 |
| 9,877,765 B2 * | 1/2018 | Barth | A61B 17/32002 |
| 10,532,410 B2 * | 1/2020 | Rinner | B23B 31/107 |
| 2018/0185035 A1 * | 7/2018 | Burk | A61B 17/32002 |

FOREIGN PATENT DOCUMENTS

| | | | | |
|---|---|---|---|---|
| DE | 102004007413 A1 * | 9/2005 | ......... | B23B 31/1071 |
| DE | 102013002818 A1 | 8/2014 | | |

OTHER PUBLICATIONS

German Search Report, Application No. 10 2018 112 681, completed: Dec. 17, 2018; dated Dec. 27, 2018, 10 pages.

\* cited by examiner

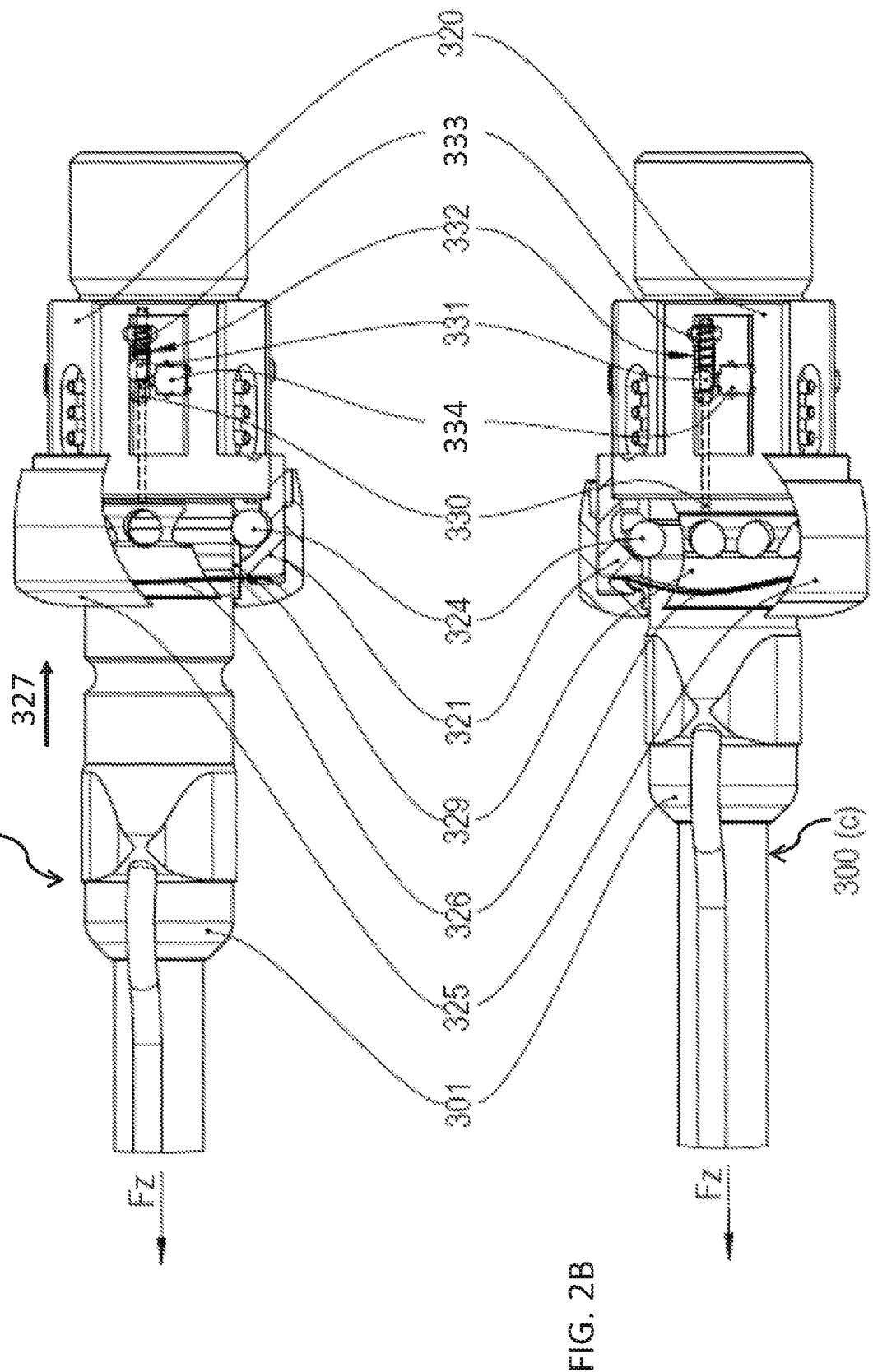

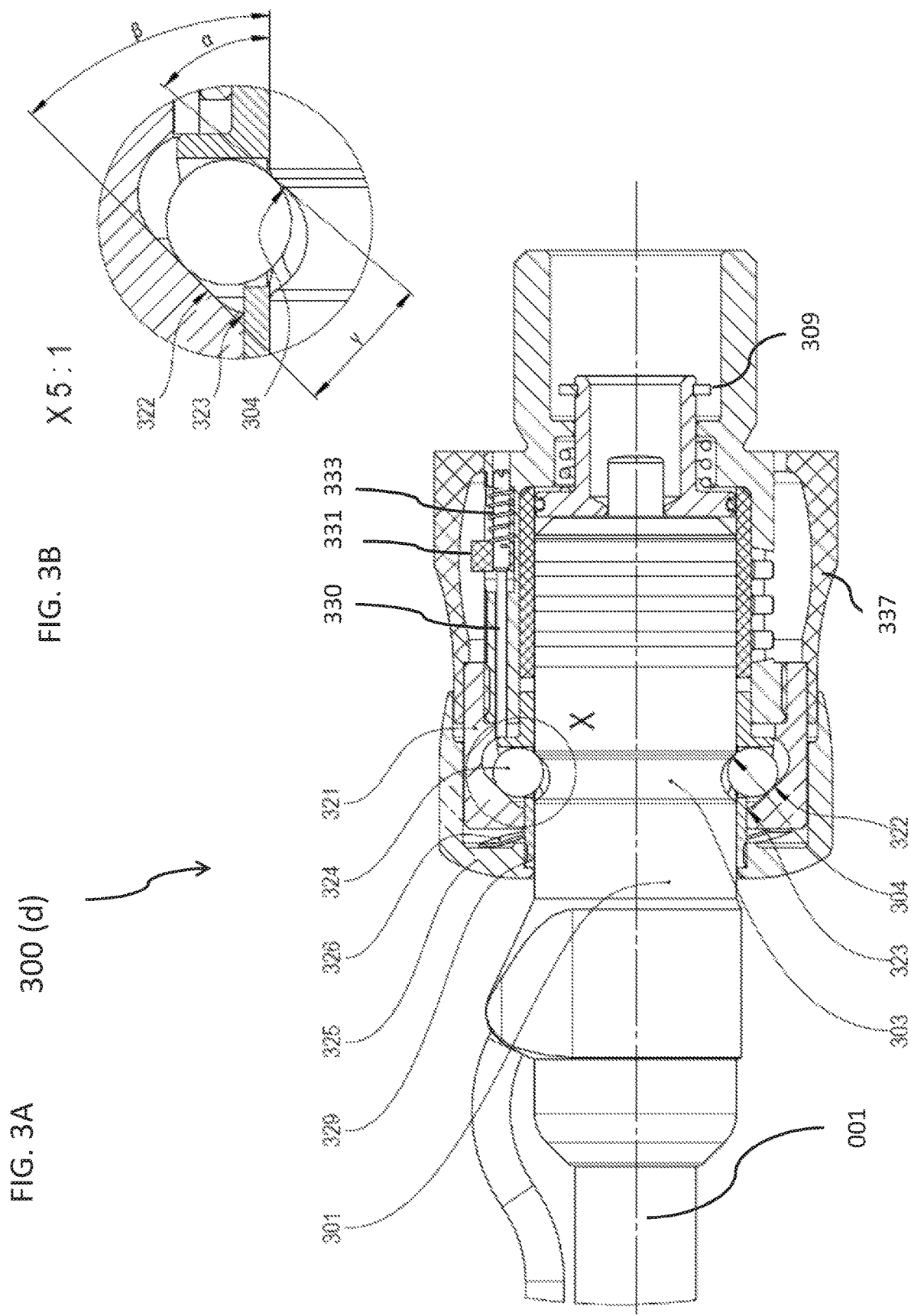

SELF-SECURING COUPLING DEVICE AND METHOD

TECHNICAL FIELD

The invention relates to a coupling device and a method for the self-securing mechanical connection of two parts of a holding system, in particular for medical uses. The invention further relates to said holding system comprising said coupling device, a holding and clamping device, which are connectable to the coupling device.

BACKGROUND

Holding systems which comprise one or more members for medical instruments, and whose parts can be connected to coupling devices, are known in a very wide variety of designs. Such holding systems are advantageous for guiding instruments particularly in minimally invasive surgery, so as to relieve an operating surgeon, an assistant or other user from tiring holding work. Surgical instruments or end effectors such as manipulators, optical aids such as an endoscope, a clamp or the like can be used at the distal end of a holding device. For medical uses, it is of great importance that end effectors and associated holding devices or holding segments can be made sterile and free of microorganisms. So that only end effectors and parts of the holding system can be autoclaved, a separation of the sterilizable parts from non-sterilizable parts of the holding system is necessary. This separation can be provided by a coupling device. The non-sterile parts of a holding system comprise, for example, elements needed for operating an end effector, such as a drive unit, power supply elements such as an accumulator, and further electronics, and can be covered with a sterile drape.

To connect parts of a holding system quickly and easily, use is generally made of releasable coupling devices with a coupling bushing and a coupling bolt. The coupling bolt, also called bolt element, should be able to be easily inserted and latched by simple pressing into the final latching or locking position. In doing so, it should not be necessary to take into account a defined rotation of both coupling halves relative to each other.

For a coupling device, it is not only important that a holding segment and the parts to be coupled can be easily connected and released again, but also that the coupled holding system permits safe and error-free operation even under loading. Disadvantages of known safety mechanisms for coupling devices arise when coupling devices are secured by additional parts, for example by cotters, securing wires or the like. Here, the user has to fit an additional element for securing the coupling connection and has to remove it again for release. In secured coupling devices of this kind, the release can in most cases be effected only with both hands or using a tool. There is also the disadvantage that, e.g. when using cotters or screw connections, there is no rotatability of the two coupling parts relative to each other. These aforementioned techniques are therefore disadvantageous when the connection is intended to be easy to manipulate or is intended to permit release with one hand or without use of tools.

SUMMARY

It is therefore an object to make available an easily releasable coupling device which has an integrated safety system. It is also an object of the coupling device to be able to transmit electrical signals and/or power between the coupling parts in the locking position. There is also the need to provide a degree of freedom of rotation of the coupled coupling device in order to be able to position an end effector optimally in a desired position. After positioning of the end effector, a holding device, and joints located therein, can be clamped or locked in the desired position with a clamping device that is connected via the coupling device. It is important here that, after locking of the holding device, a rotatability of the coupling parts relative to each other is excluded and that any torques occurring as a result of loading can be absorbed.

A further object is to make available a self-securing, load-bearing coupling device. In particular, in view of withdrawal forces that act on the coupling device during operation and can amount to several kilo newtons, there is a need to ensure that the coupling device is held in a self-securing manner in a locking position and is not inadvertently released. For this purpose, half-locked or incompletely locked states are to be ruled out. Whereas in conventional coupling devices there is the danger of a half-latched coupling device coming loose under a load, a dedicated mechanical securing means is to be made available which leads to stronger locking when a load is applied.

Moreover, it should be possible to monitor electronically whether a bolt has been inserted into the coupling bushing sufficiently to ensure that it can no longer be pulled out again under a tensile load. Particularly if the bolt is located in a so-called critical position in which the bolt is positionable under a load either in the release position or in a locking position, the risk of the bolt being inadvertently released is intended to be minimized.

It is therefore a further object of the present invention to be able to electronically determine end settings of the locking position and intermediate positions and to thereby test whether the coupling device can be loaded. Particularly in the field of medical technology with its strict safety requirements, it is an important object to ensure simple but at the same time safe transmission of force between those parts of holding systems that are to be coupled.

On the basis of the invention, the abovementioned objects are intended to be achieved more efficiently than in conventional mechanical/electromechanical instruments.

These objects are achieved with a coupling device according to the invention, a holding system comprising said coupling device, and a coupling method according to the features of the independent claims. Preferred embodiments of the invention are set forth in the dependent claims.

According to a first aspect of the invention, a coupling device for the self-securing mechanical connection of two parts of a holding system for medical instruments is made available, comprising a bolt element insertable into a bushing;

wherein the bushing has a main body and, connected fixedly to the latter, a cone sleeve which tapers conically at its free end, wherein a cage sleeve acted upon by a spring and guiding clamping bodies is inserted axially movably into the cone sleeve; wherein (a) the clamping bodies, in an uncoupled position (a), can be arranged protruding radially beyond the inner circumferential edge of the cone sleeve by means of the spring force acting on the cage sleeve;

(b) the clamping bodies, in a release position (b), are movable radially inward by displacement of the cage sleeve counter to the spring force along the cone inner face, in order to free the inner circumference of the bushing for the bolt element; and (c) the clamping bodies, in a locking position (c), can be latched into a coupling groove of the bolt element by means of the spring force;

wherein the inclined coupling groove flank, at the front in the insertion direction, of the bolt element encloses an angle α with the longitudinal axis of the bolt element;

wherein the cone inner face of the cone sleeve encloses an angle β with the central sleeve axis; and wherein, for the self-securing connection, the angle α is greater than the angle β such that clamping bodies partially or completely latched into the coupling groove can be pressed into the locking position (c) counter to the insertion direction by application of a tensile force (Fz) to the bolt element.

The cone angles α and β of the two coupling parts, i.e. the coupling groove flank of the bolt element and the bushing cone, are thus chosen relative to each other such that withdrawal forces acting on the bolt element lead to stronger locking of the coupling device. In other words, the difference angle γ between the lengthened coupling groove flank and the inclined cone inner face forms a wedge that opens in the direction of the bushing opening, as a result of which the clamping bodies always press in the direction of the bushing opening, i.e. radially inward and counter to the insertion direction of the bolt element.

The chosen angles α and β have the advantageous effect that, as soon as an operating force acts counter to the insertion direction, the clamping bodies are pressed into the clamping groove or into the locking position (c). This prevents a situation where withdrawal forces generate an inadvertent release of the coupling device. Moreover, the angles α and β, and the wedge formed by them, have the effect that clamping bodies only partially latched into the coupling groove are also latched completely in the locking position (c) by the operating force. A self-securing coupling device is thus made available without additional securing elements such as cotters, which coupling device does not come loose despite high tensile forces Fz.

According to a further aspect of the invention, the difference (γ) of the angles is between 1° and 15°. Although a small difference of just 1° suffices for the self-securing mechanism, differences of at least 5° can preferably be chosen in order to take account of possible manufacturing tolerances and safety allowances.

According to a further aspect of the invention, the angle α of the front inclined coupling groove flank of the bolt element encloses an angle of between 5° and 60°, preferably 25°, and the angle β of the cone inner face encloses an angle of between 10° and 55°, preferably 20°. How flat or steep the chosen angles are depends additionally on factors such as release force and surface pressure of the clamping bodies.

According to a further aspect of the invention, the coupling device moreover has a switching element in order to determine the clamping body position and to exclude a critical position (d) of the clamping bodies in which, after application of a tensile force (Fz) to the bolt element, the clamping bodies can be pressed either into the release position (b) or locking position (c); wherein the critical position (d) of the clamping bodies is located in the region between the inner circumferential edge of the cone sleeve and the outer circumferential edge of the coupling groove; and wherein, by means of the switching element, the application of tensile force (Fz) to the bolt element can be enabled only when the clamping body position that has been determined is a position beyond the critical position (d), wherein the clamping bodies are positioned partially or completely latched on the bolt element in the locking position (c).

If the bolt element is not inserted completely, the clamping bodies can latch incompletely and can be positioned in said critical position (d), such that there is the danger of the coupling device being unable to transmit tensile forces and inadvertently coming loose in an uncontrolled manner. Since operating persons cannot ascertain said critical position (d), the switching element, which can be configured as a microswitch or button or the like, is used. Thus, the switching element can serve as a monitoring unit and advantageously exclude the application of tensile force to the coupling device in the critical position. Thus, a critical position (d) is practically no longer possible, and only stable, load-bearing positions are allowed for application of force. Said stable positions can be the completely latched clamping body position in the locking position (c), or partially latched positions beyond the critical position (d), in which the clamping bodies press into the locking position on account of the self-securing mechanism under a tensile load.

According to a further aspect of the invention, the main body has a plurality of guide gaps in each of which a switching element designed as a switching pin is axially movable by means of the cage sleeve, wherein each switching pin has a switching cam at its free end in order to actuate a limit switch for enabling a tensile force (Fz) according to the position of the clamping bodies.

The guiding of the switching elements or switching pins in guide gaps permits a compact and at the same time secure monitoring unit. Each limit switch monitors whether the coupling device is also fully mechanically locked. By virtue of a tensile force being enabled in a controlled manner by switching elements, a holding device attached via the coupling device cannot be inadvertently released and thus get out of control.

To be able to reliably prevent application of force in a critical position of the coupling device, the evaluation of the positions is a redundant evaluation, i.e. with at least two switching elements or sensors which are preferably distributed uniformly with respect to the circumference of the bushing. The redundant monitoring by means of a plurality of switching elements is of importance particularly in the field of medical technology in order to be able to exclude possible dangers posed to the operating persons, and also to the patients being treated, by inadvertent release of the coupling device.

According to a further aspect of the invention, the limit switches are surrounded by a transparent cover element which has at least one lighting element in order to provide light in accordance with the actuation of the limit switches.

On the one hand, the cover element serves as a housing and protects the switching mechanism and the contact elements from soiling and damage. On the other hand, the at least one lighting element under the cover element serves as a signal indicator by lighting up in accordance with the actuation of the limit switch. The lighting element can comprise one or more LEDs arranged next to an associated limit switch. The cover element is produced, for example, as a ring made of transparent or milky plastic. In this way, it is possible to indicate to an operating person whether or not stable clamping body positions or positions beyond the critical position (d) are present.

According to a further aspect of the invention, the coupling device moreover has an actuation element connectable to the cage sleeve, wherein the cage sleeve guiding the clamping bodies is movable, by means of the actuation element, to the release position counter to a spring force of spring means which are arranged between the cone sleeve and the actuation element.

With the aid of the actuation element preferably fixedly connected to the cage sleeve, the coupling device can be brought without tools from the locking position (c) to the release position (b) for dismantling. If a holding device in the form of an arm with a joint to the coupling device is to be decoupled, the dismantling can be done with one hand with the aid of the actuation element. For controlled release of the coupling device, the holding device should not be locked, such that no tensile force acts on the coupling device and a force flow for example between a clamping device and the holding device does not have to be interrupted. This means that both the release and also the connection of a holding device to the coupling device takes place without application of force with the holding arm not locked or released. When the joint of the arm is released, however, it is necessary that a hand is located at the distal handle of the holding device in order to prevent uncontrolled shaking of the holding arm. The other hand can then operate the actuation element of the coupling device for release.

According to a further aspect of the invention, the actuation element is designed as an actuation ring and the spring means are designed as a wave washer.

The wave washer is easy to mount and acts between the actuation element and the cone sleeve.

According to a further aspect of the invention, the coupling device moreover has an ejector spring in order to eject the released bolt element in the release position (b), such that re-engagement of the clamping bodies in the coupling groove is prevented.

In other words, the ejector spring presses on the ejector bolt counter to the insertion direction, in order in this way to prevent inadvertent re-engagement in the locking position (c).

According to a further aspect of the invention, the bolt element and the bushing are freely rotatable relative to each other.

In this way, a rotation of the coupling parts in the released state of the holding device takes place smoothly, such that an operating person can bring the holding device and attached end effectors or the like to a desired position. Too smooth a rotation can be disadvantageous for handling and for precise positioning, such that, according to an advantageous embodiment of the coupling device, a certain residual inhibition is provided.

By contrast, when a load is applied or when a clamping force is transmitted between the coupling parts from a proximal pushing element to a distal pushing element, the rotatability of the coupling parts relative to each other is suppressed and a rotationally fixed connection is produced in order to reliably maintain the chosen position of an attached holding device. Tensile forces acting on the coupling device can be introduced, for example, from a proximal pushing element, drivable by a spindle, to a distal pushing element which is guided axially in the coupling bolt. The pushing element guided in the coupling bolt and in the holding segment of the holding device has the least possible play or angular offset along the axis, in order, for the purpose of optimal force transmission, to lose the least possible travel through axial play or relative movements. While the inner pushing element of the holding device presses in the distal direction for clamping or locking the joint, the coupling device is designed to counter the outer tube of the holding segment, attached to the coupling device, with the same force.

According to a further aspect of the invention, the clamping bodies are designed as balls, barrel rollers or cylinder rollers.

To be able to generate a certain residual inhibition, barrel rollers or cylinder rollers can be used instead of balls. The clamping bodies can also preferably be designed as barrel rollers in order to support a complete rotationally fixed fastening of the coupling device under a load.

According to a further aspect of the invention, at least one contact face for electrically connecting a signal line to at least one contact element of the main body is formed at the end of the bolt element.

In this way, the coupling device in the locking position can transmit electrical signals and/or power between the coupling parts. The at least one contact face is preferably ring-shaped, in order to be able to transmit electrical signals and/or power in each position of the bolt element freely rotatable when no load is applied.

In order to transmit electrical signals, a cable is advantageously introduced into the coupling bolt and the at least one line is connected to the contact face preferably configured as a gold-plated slip ring. In this way, electrical signals or power can be reliably transmitted between the coupling parts. For example, a switching signal for actuation of a clamping device can be delivered. Moreover, the at least one or more electrical connections can also function as a monitoring unit. As soon as the electrical connection between bolt and bushing is produced, there is also a perfect and secure connection between the coupling parts. Therefore, with the aid of the at least one contact face and associated contact element of the coupling, it is possible to check electrically whether the operating power can be enabled for clamping or locking the attached holding device. This electrical check can be used additionally or alternatively to the above-described monitoring unit with switching elements and limit switches. In this way, fully mechanical locking can be ensured before the coupling device is loaded.

According to a further aspect, a plurality of contact faces, and a plurality of contact elements insulated from one another via an insulating sleeve, are made available, and each contact face of the bolt element is electrically connectable to a respective contact element of the main body.

With the aid of such an electrical interface, a plurality of signals or power can be transmitted.

According to a further aspect of the invention, a coupling device comprises a holding system, wherein a first part of the holding system is a clamping device and a second part of the holding system is a holding device for medical instruments.

Advantageously, embodiments of the coupling device go together with and thus function with parts or holding segments of holding devices or clamping devices. Thus, the main body of the coupling device can be connected, for example, to the free end of a clamping device, wherein a movable pushing element in the interior of the holding segment of the clamping device can interact with an axially movable pushing element of the coupled holding device. Furthermore, the embodiments of the coupling device go together with already existing tools.

The coupling device is advantageously designed such that it can quickly couple the holding device to the clamping device and quickly uncouple or release it. For safety purposes, the coupling device is not releasable during operation, i.e. under a load, even if great forces act on it during the operation of the holding device. The maximum loading is reached when the holding device, which is preferably designed as a holding arm with a central joint, is extended horizontally and thus attains the greatest reach. In this position, the holding system according to the invention can attain holding forces of for example between at least 3 kg and 5 kg. Examples of the reaches of the entire holding system are preferably between 55 cm and 71 cm.

For uses in sterile environments, it is necessary to release the holding device or the holding arm from the coupling device in order to sterilize it. Parts of the holding system that are not provided for sterilization, such as coupling device and clamping device, can be covered with a suitable sterile cover or drape.

According to a further aspect of the invention, the main body of the bushing is designed such that the end of an axially displaceable pushing element of the clamping device can be arranged protruding into the main body. Moreover, the bolt element is connectable to a proximal holding segment of the holding device such that the proximal end of a pushing element displaceable in the holding segment and in the bolt element can be arranged protruding beyond the front side of the bolt element. Furthermore, in the locking position (c) of the coupling device, and by means of the pushing element of the clamping device displaceable via a spindle, the proximal end of the pushing element of the coupled holding device is axially displaceable counter to the insertion direction of the bolt element to permit locking with frictional engagement.

A spindle drive or the like is advantageously provided as a drive unit for the relative displacement of the proximal pushing element of the clamping device. These drives permit simple control of the relative displacement since they can be actuated both by one hand and also by means of a motor. By means of a distal actuation element on the holding device, the motor can be actuated via the electrical connections in the coupling device. In this way, the spindle and thus the pushing element can be operated automatically with a single actuation signal. The pushing element of the clamping device can be fixedly connected to the spindle or can be formed in one piece therewith. If an electric motor is used for the spindle drive, the clamping device has the associated switching logic, the control unit and power supply (preferably an accumulator), wherein the operation of the drive unit is possible only when a monitoring unit and a switching element determine a complete locking position (c) of the coupling device.

Moreover, a method for the self-securing mechanical connection of two parts of a holding system for medical instruments is made available, comprising the following steps: making available a coupling device with a bolt element insertable into a bushing, wherein the bushing has a main body with a cone sleeve connected fixedly thereto, wherein a cage sleeve acted upon by a spring and guiding clamping bodies is used which can be moved axially between the positions (a), (b) and (c); wherein (a) in the uncoupled position (a), the clamping bodies protrude radially beyond the inner circumferential edge of the cone sleeve by means of the spring force, (b) in the release position (b), the clamping bodies are moved radially inward by displacement of the cage sleeve counter to the spring force along the cone inner face, in order to free the inner circumference of the bushing for the bolt element; and (c) in the locking position (c), the clamping bodies can latch into a coupling groove of the bolt element by means of the spring force;

when a tensile force (Fz) is applied to the bolt element, clamping bodies partially or completely latched into the coupling groove are pressed into the locking position (c) counter to the insertion direction, since the angle $\alpha$ of the front inclined coupling groove flank of the bolt element is greater than the angle $\beta$ of the cone inner face of the cone sleeve.

With the aid of the angle difference $\gamma$ of $\alpha$ and $\beta$, i.e. by means of the wedge angle that opens into the bushing opening between the inclination axis of the coupling groove flank and the inclination axis of the cone inner face, the clamping bodies are pressed into the locking position (c) under a load. In this way, a self-securing method for a coupling device is made available, and half-latched coupling devices cannot inadvertently come loose. This increases the safety of the coupling device.

The method moreover comprises the following method steps:

determination of the clamping body position by means of a switching element in order to exclude a critical position (d) of the clamping bodies in which, after application of a tensile force Fz to the bolt element, the clamping bodies can be pressed either into the release position (b) or locking position (c); and wherein, by means of the switching element, the application of tensile force Fz to the bolt element is enabled only when the clamping body position that has been determined is a position beyond the critical position (d), wherein the clamping bodies are positioned partially or completely latched on the bolt element in the locking position.

It is ensured in this way that the clamping bodies on the bolt element latch completely under a load and adopt the locking position (c).

At least one of the above aspects and embodiments represents one or more solutions to the problems and disadvantages of the prior art. Other technical advantages of the present disclosure will be clear to a person skilled in the art from the following description and from the patent claims. Each claimed embodiment can be combined technically with any other claimed embodiment or with any other claimed embodiments.

BRIEF DESCRIPTION OF THE DRAWINGS

Further advantages and features of the invention will become clear from the following description of illustrative embodiments and by reference to the figures, in which:

FIG. 2A shows a isometric view of a coupling device according to the invention in the release position (b), wherein partial sectional views illustrate elements of the bushing;

FIG. 2B shows the coupling device from FIG. 2A in a locking position (c), with partial sectional views;

FIG. 3A shows a sectional view of a coupling device according to the invention in the critical position (d);

FIG. 3B shows a detail of FIG. 3A at the level of the coupling groove;

The illustrations are schematic and not necessarily true to scale. Moreover, they do not show all the particulars and are instead restricted to showing the features that are essential to the invention and also further features that facilitate the explanation and description of the invention. Identical elements in the different figures are designated by identical reference signs.

DETAILED DESCRIPTION

Figure 1A:
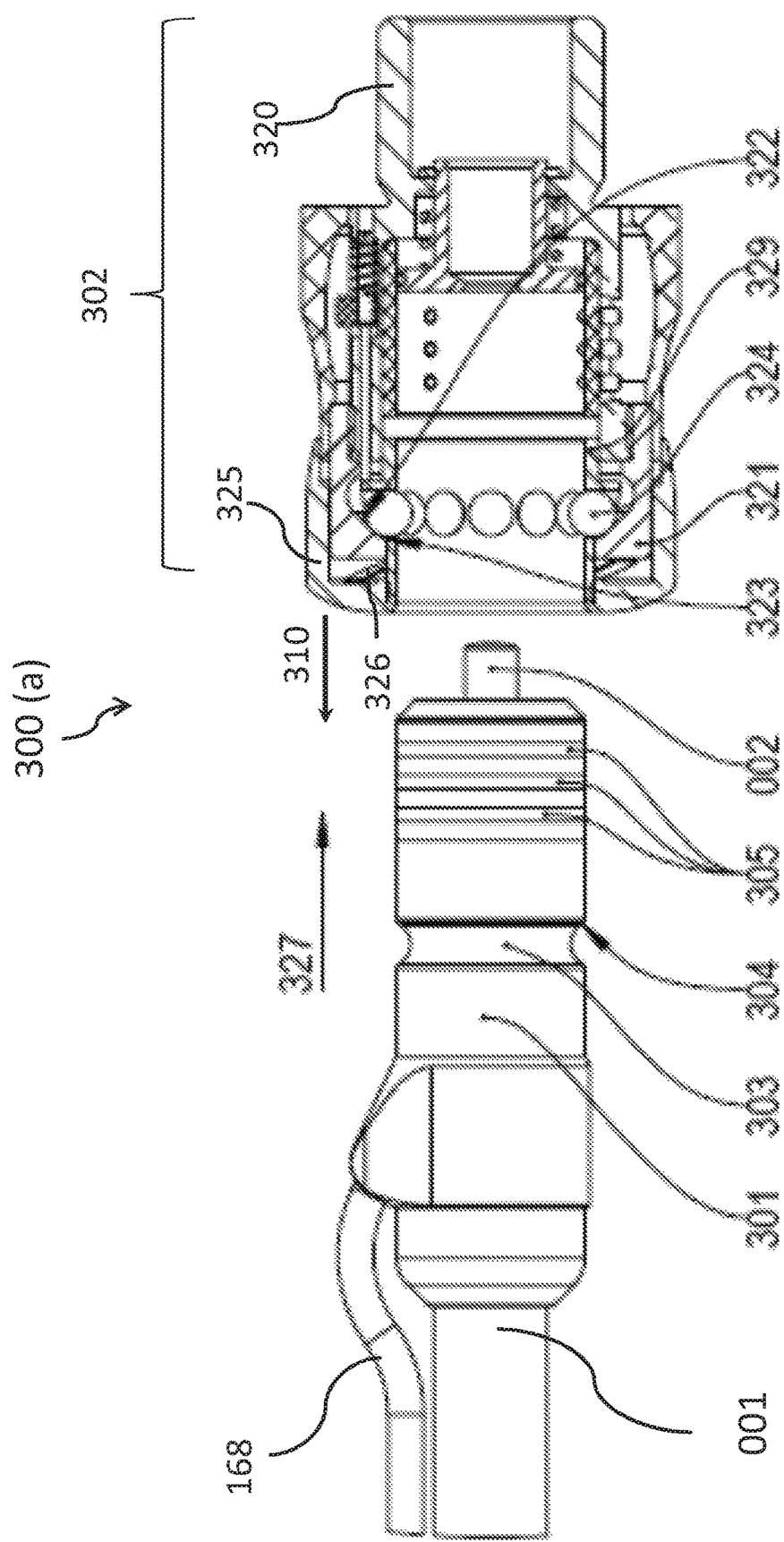
FIG. 1A shows a schematic sectional view of a coupling device in the uncoupled position (a)
Figures 1B, 1C:
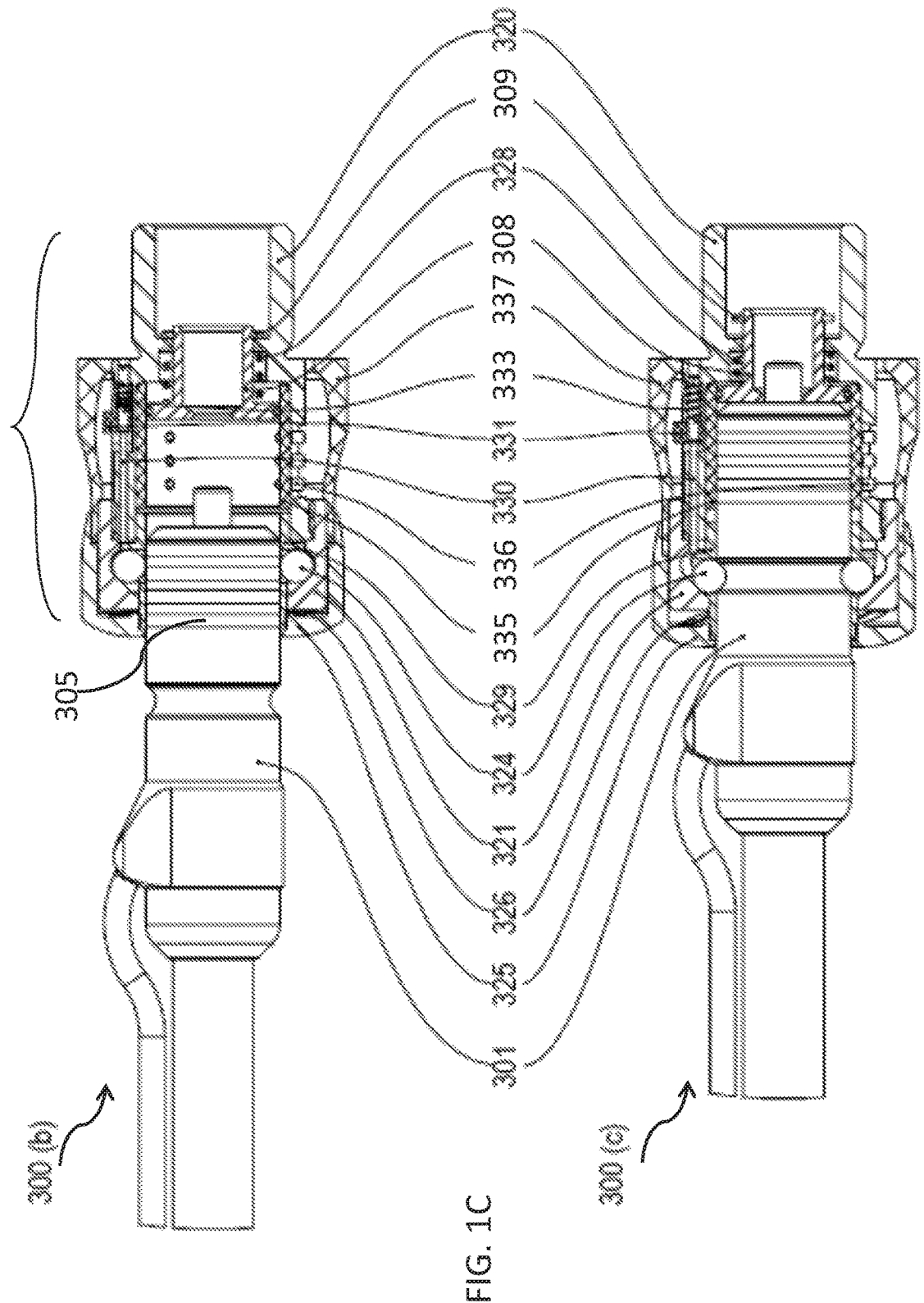
FIG. 1B shows the coupling device shown in FIG. 1A in the release position (b)
FIG. 1C shows the coupling device from FIG. 1A and FIG. 1B in a locking position (c)

FIG. 1A, FIG. 1B and FIG. 1C show a coupling device 300 according to one embodiment in different positions. FIG. 1A shows an uncoupled position (a), FIG. 1B shows a release position (b), and FIG. 1C shows a locking position (c) of the coupling device 300 (a, b, c). The coupling device 300 is composed principally of two parts that are to be connected, on the one hand the bolt element 301, and on the other hand the bushing 302, which is designed to receive the bolt element 301. The main elements for the self-securing mechanism of the coupling device of the bolt element 301 are the coupling groove 303, and the cone face of the bolt 301 inclined on the right-hand groove flank 304, and the clamping bodies 324 running along said surfaces.

The bolt element 301 is connected to a holding segment 001 in which an axially displaceable pushing element 002 is arranged which protrudes beyond the end of the bolt element 301. The bolt element 301 can be inserted in the direction of the arrow 327 (insertion direction) into the bushing 302 and coupled and can be decoupled in the ejection direction 310.

Several electrical signals and, if appropriate, power are intended to be reliably transmitted between the coupling parts after coupling. For this purpose, a plurality of contact faces 305 are located at the free end of the bolt element 301. The contact faces 305 are ring-shaped and form a slip ring group, in order to be able to transmit electrical signals and/or power in each position of the bolt element. A cable 168 is inserted into the coupling bolt and the respective lines are connected to the individual contact faces 305 in order to be able to transmit electrical signals or power between the coupling parts. For example, a switching signal in the locking position (c), for actuation of a clamping device 100 connected to the main body 320, can be forwarded in order to displace the axially displaceable pushing element 002 for clamping or locking a joint attached to the holding segment 001.

The bushing 302 is composed principally of a main body 320, which is connectable to a cone sleeve 321. The main body 320 and the associated cone sleeve 321 form the unmoved part of the bushing 302. The cage sleeve 329, which for its part is fixedly connected to an actuation element 325 in the form of an actuation ring, is located axially movably therein. Spherical roller bodies 324 are guided in the cage sleeve 329. They can also be configured as barrel roller bodies or as cylinder rollers.

The roller bodies serve as clamping bodies 324. Spring means 326 in the form of a wave washer press the cage sleeve 329 together with the actuation element 325 constantly in the direction of the arrow 310 (toward the left in the figure) counter to the insertion direction 327. By way of the spring-loaded cage sleeve 329, the clamping bodies 324 are likewise pressed in the direction of the bushing opening (see arrow 310) and run along the cone inner face 322. On account of the inclination of the cone inner face 322, the clamping bodies are pressed not only toward the left (arrow 310) but also radially inward. By means of the spring force acting on the cage sleeve 329, the clamping bodies 324 are thus positioned protruding radially beyond the inner circumferential edge 323 of the cone sleeve 321. In the uncoupled position (a) shown, the clamping bodies 324 not only protrude above the edge 323 of the cone sleeve 321 but also through the openings of the cage sleeve 329.

When the free bolt end of the bolt element 301 is moved into the bushing 302 in the insertion direction 327, the coupling device 300 is initially located in the release position (b) shown in FIG. 1B (reference sign 300(b)).

In the uncoupled position (a), which is shown in FIG. 1A, the clamping bodies 324 are pressed, as far as the cage sleeve 329 permits, in the direction of the arrow 310 and into the interior of the bushing, such that the clamping bodies 324 protrude far into the interior of the bushing 302. After the bolt element 301 has been inserted into the bushing, as is shown in FIG. 1B, the bolt element bears on the protruding clamping bodies 324 and pushes these, together with the cage sleeve 329, in the insertion direction 327. The clamping bodies 324 can run along the cone inner face 322 and out through the widening cone and thus free the internal diameter of the bushing 302. In this way, the bolt element 301 can be pushed fully into the bushing 302. This state of complete locking or the so-called locking position (c) is shown in FIG. 10.

FIG. 1C shows the so-called locking position (c), where the bolt element 301 has been inserted fully into the bushing 302. In the illustrated state of the locking position (c), the clamping bodies 324 are latched far or to the maximum extent into the coupling groove 303 of the bolt element. After the bolt element 301 has been fully pushed in, the coupling groove 303 is positioned such that the clamping bodies 324 can be pressed into the groove. The spring means 326 then have the task of moving the clamping bodies 324, again counter to the insertion direction, in the direction of the arrow 310 (here to the left in the ejection direction). In this way, the coupling is locked and the clamping bodies 324 are located in the locking position (c).

In the locking position (c) shown, considerable tensile forces Fz can act on the bolt element in the direction 310, i.e. toward the left. To avoid the bolt element 301 being accidentally released or the coupling device 300 coming loose in an uncontrolled manner, the angles $\alpha$ and $\beta$ at the coupling groove flank of the bolt element 301 and at the cone inner face 322 of the bushing 302 were chosen such that the front inclined coupling groove flank 304 of the bolt element 301 in the insertion direction 327 has a greater angle $\alpha$ than the inclination 13 of the cone inner face 322 of the cone sleeve 321. This is shown in detail in FIG. 3B.

FIG. 1C moreover shows electrical elements of the coupling device 300. In the locked position 300 (c) shown, the contact faces 305 of the bolt element 301 can provide an electrical connection to corresponding contact elements 336 of the bushing 302. The contact elements 336 are insulated from one another via an insulating sleeve 335. In this way, each contact face 305 of the bolt element 301 can be electrically connected to a respective contact element 336 of the main body 320. In other words, the insulating sleeve 335 receives the contact elements 336 of the bushing and insulates these from one another. Any suitable non-conductive material can be used here as insulating material. In this way, it is possible not only to provide a signal line for the actuation of an attached clamping device 100 but also a power supply for distally attached medical instruments.

The coupling device 300 has a switching mechanism with switching elements 330 for determining the clamping body position and in particular for excluding a critical position (d) of the clamping bodies 324 in which, after application of a tensile force Fz to the bolt element 301, the clamping bodies 324 can be pressed either into the release position (b) or locking position (c). FIGS. 1A-1C and the isometric views of FIGS. 2A and 2B show a switching mechanism in which the main body 320 has a plurality of guide gaps 332 in each of which a switching element 330 configured as a switching pin is axially movable by means of the cage sleeve 329 in cooperation with a switching spring 333 (in FIGS. 2A and 2B, reference sign 332 shows an example of a guide gap in which a switching element 330 indicated by dashed lines is guided). At its free end, each switching pin or switching element 330 has a switching cam 331 in order to actuate a limit switch 334 (reference sign 334, see FIGS. 2A and 2B) for enabling application of tensile force in accordance with the position of the clamping bodies 324.

The redundant switching elements 330 are pressed constantly against the cage sleeve 329 with the aid of a switching spring 333 in order to exclude incorrect actuations of the limit switch 324 in unlocked or uncontrollably partially latched positions. When the clamping bodies in the locking position (c) snap fully into the coupling groove 303, the cage sleeve 329 has been displaced to the left to the maximum extent and the switching spring 333 presses the respective switching cams 331 at the level of the limit switch 334 (see clamping device 300(c) in FIG. 2B). The switching mechanism with its components (cf. reference signs 330, 331, 332, 333 and 334) is illustrated in different views or clamping body positions in FIGS. 1A, 1B, 1C, FIGS. 2A, 2B and FIG. 3A and FIG. 4.

A cover element or luminous ring 337 (see, for example, FIG. 1B or 1C or FIG. 3A) is provided as a housing of the bushing. On the one hand, this luminous ring has the function of protecting the switching mechanism and, on the other hand, the luminous ring 337 can advantageously be used as a signal display. In this case, the luminous ring 337 is produced from a transparent or milky plastic, and a suitable lighting element is mounted which can emit light behind the luminous ring 337. The lighting element can comprise one or more LEDs which are each arranged beside an associated limit switch 334. In this way, it is possible to indicate to an operating person whether or not stable clamping body positions or positions beyond the critical position (d) are present.

It is only when the limit switches 334 are actuated on account of the clamping body positions that it is possible for a tensile force Fz to be applied and for the relevant clamping body positions to be indicated to an operating person advantageously by said lighting elements. For this purpose, the lighting elements can light up in different colors (e.g. green/red) or with a different lighting duration (e.g. steady light/flashing light). In this way, the switching mechanism can be used together with the lighting element to ensure that an operating person activates a force application in the direction of the tensile force Fz (see FIG. 2A or 2B) only when the clamping bodies 324 are locked fixedly beyond a critical position or the bolt element 301 is fixedly locked.

To release the two coupling parts of the bolt element 301 and of the bushing 302, the locking position (c) can be transferred to the release position (b) via an actuation element 325. The ejector spring 328 (see FIGS. 1B and 1C) is made available in order to eject the released bolt element 301 in the release position (b), such that re-engagement of the clamping bodies 324 in the coupling groove 303 is prevented. The securing ring 309 (see FIGS. 1B and 1C, FIG. 3B or FIG. 4) prevents the ejector bolt 308 from being flung completely out of the coupling device 300 by the ejector spring 328.

FIG. 2A and FIG. 2B show the actuation ring 325 or actuation element for the coupling device 300 in a isometric partial view. The actuation element 325 can simply be displaced by hand in the insertion direction 327. In the views shown, the actuation ring or actuation element 325 is pressed toward the right in order to generate the release from the locking position (c). The clamping bodies 324 are thereby likewise pushed by the cage sleeve 329 toward the right, or in the direction of the arrow 327, and can deflect radially outward or in the direction of the main body 320 inside the bushing cone along the cone inner face 322 or in the cone sleeve 321. Thus, the clamping bodies 324 no longer lie in the coupling groove 303, and the bolt element 301 can be removed from the bushing 302 in this release position (b) (see FIG. 2B for example).

For the reliable release of the coupling device 300, an ejector spring 328 (shown in FIG. 1 or FIG. 4 for example) automatically presses the released bolt element 301 a short distance out of the coupling device 300, such that the clamping bodies 324 do not latch again when the user lets go of the actuation ring or the actuation element 325. A securing ring 308 prevents the ejector bolt from being pressed too far in the direction of the bushing opening. As is shown in the sectional views in FIGS. 1A-C and the exploded view in FIG. 4, the ejector bolt 308 for the bolt element 301 is hollow in order to guide a pushing element 118 (shown in FIG. 5 for example) of an attachable clamping device 100 through the opening.

FIG. 3A shows a sectional view of the coupling device 300 in the critical position (d), and FIG. 3B shows a detail of the coupling groove 303 in order to illustrate the position of the clamping bodies 324 in the critical position (d). The clamping body 324 shown is located here in the region between the inner circumferential edge 323 of the cone sleeve 321 and the outer circumferential edge of the coupling groove 303. This means that the clamping body 324 shown by way of example is positioned exactly at the edge to the inclined coupling groove flank 304.

The enlarged view according to FIG. 3B illustrates that the angle $\alpha$ of the inclined coupling flank 304 is such that it is greater than the angle $\beta$ enclosed by the cone inner face 322 with the central sleeve axis. Moreover, the angle $\gamma$ indicates the difference between the shown angles $\alpha$ and $\beta$. This difference between the inclination of the coupling groove flank 304 and the inclination of the cone inner face 322 should advantageously be between 1° and 15°, preferably 5°. The angles $\alpha$ and $\beta$, which span a difference angle $\gamma$ and thus a wedge that opens toward the bushing opening, have the effect, together with the spring force of the spring element 326, that the clamping bodies 324 always press in the direction of the latching position or locking position (c) when a tensile force Fz acts on the bolt element 301 counter to the insertion direction. The cone angles $\alpha$ and $\beta$ of the two coupling parts (301, 302), in particular of the coupling groove flank 304 of the bolt element 301 and of the cone inner face 322 of the bushing, are chosen in relation to each other such that withdrawal forces Fz lead to stronger locking of the coupling device. In this way, a self-securing coupling method can be made available.

As has been described above, the potentially dangerous critical point (position (d)) between locking and release is detected by a limit switch 324 and can thus exclude a force application Fz and can prevent release happening inadvertently. If a holding device 20 and then additionally instruments are attached to the coupling device 300, high withdrawal forces Fz, amounting to several kN depending on the position, can act during operation. However, by virtue of the self-securing coupling device 300, it is not possible for the coupling device 300 according to the invention to come loose when subjected to a high tensile force Fz. The strict safety requirements in medical applications are thus satisfied.

Figure 4:
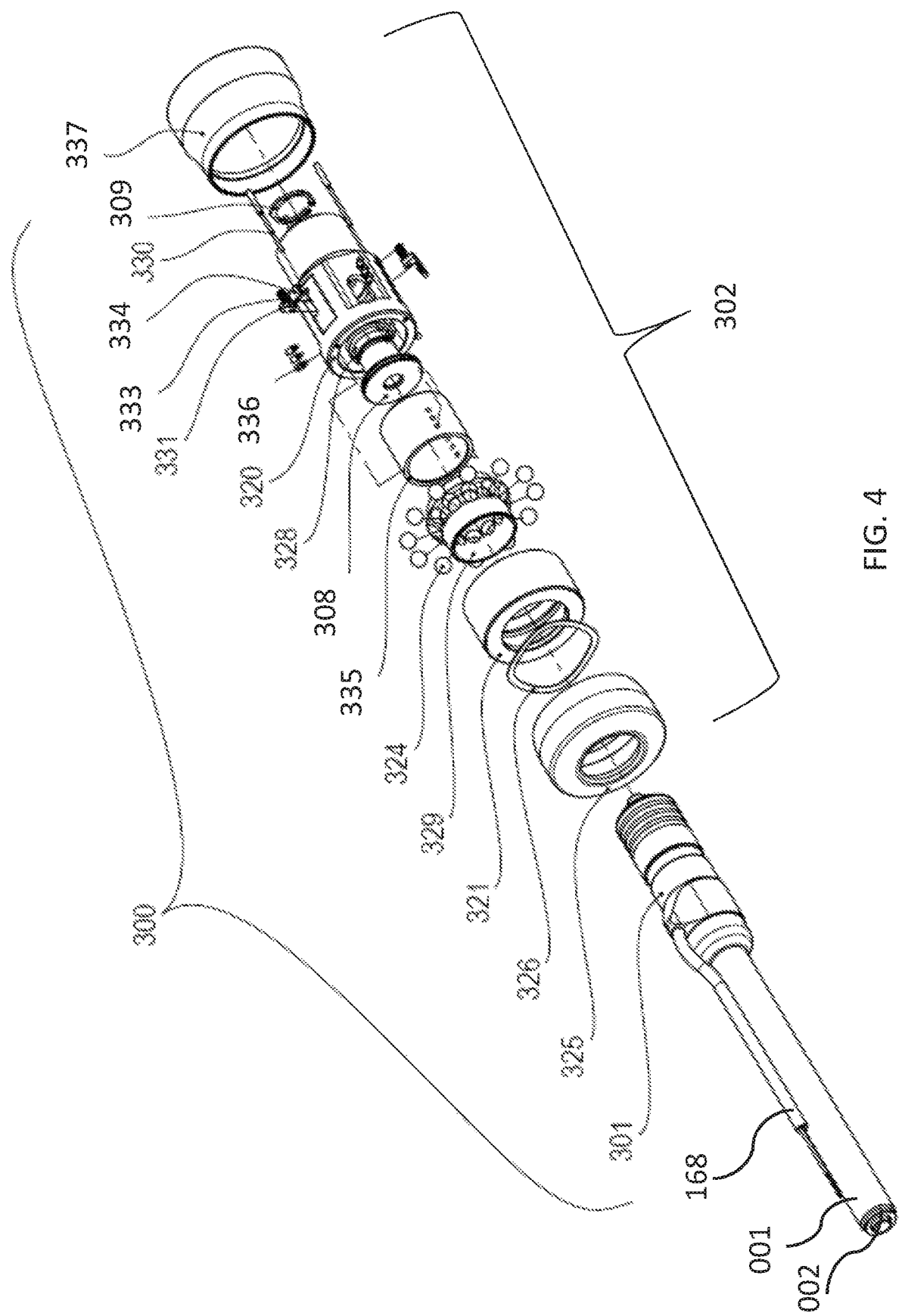
FIG. 4 shows a isometric exploded view of a further embodiment of the coupling device.

The exploded view in FIG. 4 shows all the elements of the coupling device 300, in particular of the bolt element 301 and of the bushing 302, in a isometric view. A cable 168 with a plurality of electrical lines is inserted into the bolt element 301. The axially displaceable pushing element 002 is guided with the least possible play in the interior of the bolt element 301 and of the holding segment 001.

As regards the bushing 302, it is further shown that a plurality of openings for the respective clamping bodies 324 are made available about the entire circumference of the cage sleeve 329. It is additionally shown that the ejector bolt 308 is not only hollow but also has a flank in order to exert pressure on the bolt element 301 in the release position (b) with the aid of the ejector spring 328. The securing ring 309 prevents the ejector bolt 308 from being flung completely out of the bushing 302 by the ejector spring 328.

As has already been explained, a plurality of electrical signals can be reliably transmitted by the coupling parts 301 and 302. The insulating sleeve 335 is designed to insulate the contact elements 336 of the main body from one another (three openings are shown here by way of example in FIG. 4).

The switching mechanism is further illustrated with three switching elements 330, switching cams 331 and limit switches 334 distributed uniformly with respect to the circumference of the main body. Each switching element is pressed constantly against the cage sleeve 329 with the aid of a switching spring 333 (see also the preceding figures, e.g. FIG. 3A), such that the switching elements 330 designed as switching pins actuate the respective limit switches 334 only in positions beyond the critical position (d).

It is a significant safety advantage that, by means of the redundant number of switching elements and associated limit switches, it is possible to reliably determine the coupling state, i.e. whether the locking position (c) or the critical clamping body position (d) is present.

Figure 5:
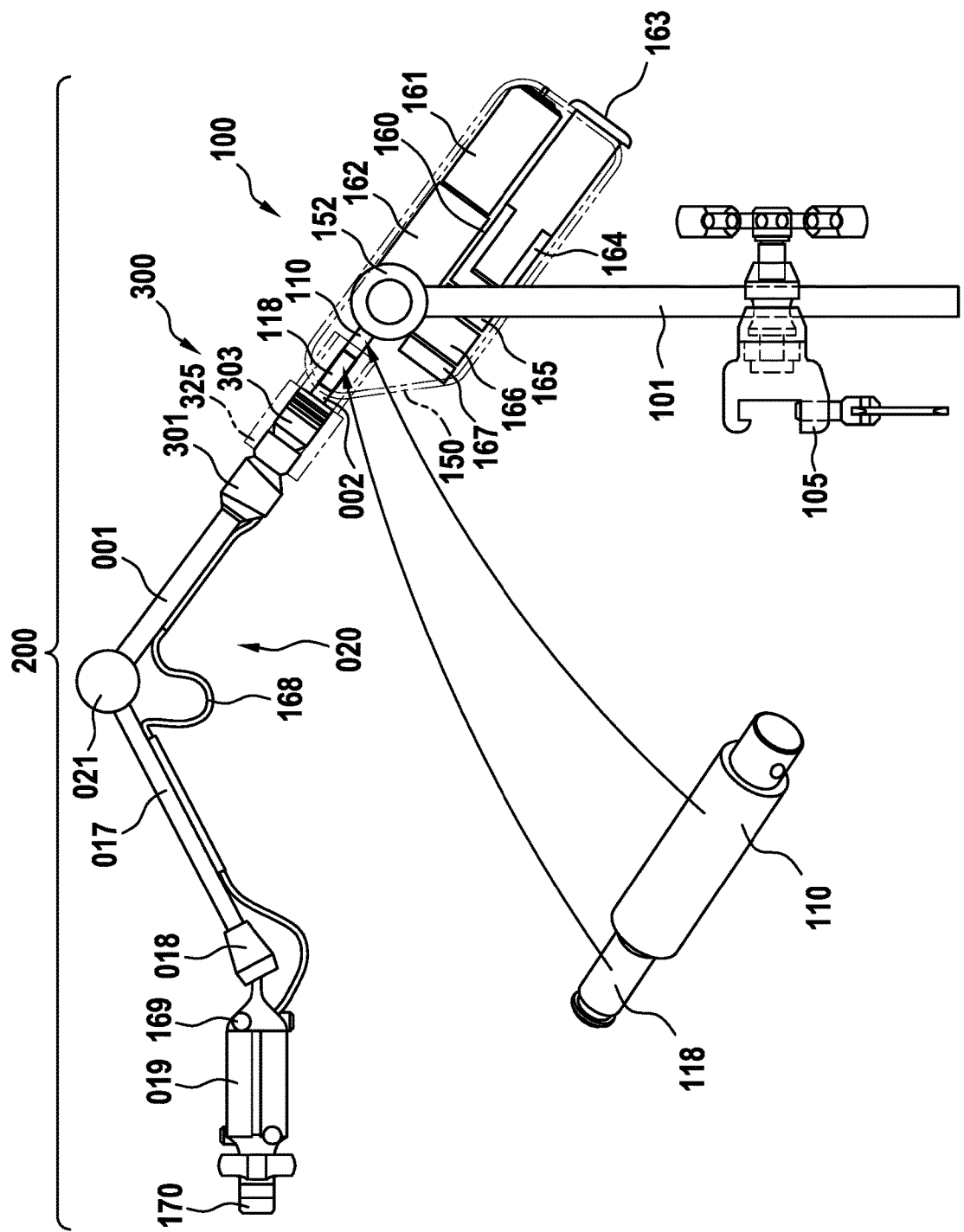
FIG. 5 shows a schematic isometric view of a holding system with a further embodiment of a coupling device, which connects a proximal clamping device to a distal holding device, and a detailed view of a spindle of the clamping device.

The isometric view in FIG. 5 shows a holding system 200 and a isometric detail of a spindle 110 of a clamping device 100. By means of the coupling device 300, the holding system 200 shown connects proximally a clamping device 100 and distally a holding device 20. Upon connection to the clamping device 100, the proximal side of the main body 320 of the coupling device 300 can receive centrally a pushing element 118 of a spindle 110. The spindle 110 is designed to axially displace the pushing element 002 of the attached holding device 20 with the aid of the pushing element 118. By this axial displacement of the pushing elements 118, 002 in a distal direction, joints of the holding system 200 can be reliably clamped or locked. The detailed view of the spindle 110 shows that the pushing element 118 is connected fixedly to the spindle 110. The spindle 110 and the pushing element 118 can also be configured in one piece and designated as pressure spindle.

With respect to the clamping device 100 of the holding system 200, FIG. 5 shows a base column 101. This base column or holding segment 101 is compatible with all existing and commercially available clamp units 105, such that it can be securely clamped to an operating table for medical applications. The base column or the holding segment 101 can have a diameter of about 16 mm, for example. Larger diameters of up to a maximum of 2 cm can also be made available for a particularly large payload.

The fastening point of the clamp unit 105 for the first holding segment 101 is arranged in the proximal region of the clamping device 100. The proximal region can be located near the floor or an operating table. Alternatively, the holding system 200 can be mounted on the ceiling, in contrast to a system supported on an operating table. The distal region of the holding system 200 is the region remote from the proximal region. At the distal side of the clamping device 100, a holding device 20 in the form of a holding arm with upper arm and lower arm is attached via the coupling device 300. The attached holding device 20 comprises two holding segments 001 and 017, which are connected pivotably to each other by a central joint 21.

The clamping device 100 has a housing 150. For the pivotability of the holding segment or base column 101, a (base) joint 152 is located between the housing of the clamping device 100 and the holding segment 001, which joint 152 can also be called a shoulder joint on account of the arm-like holding device 20 attached distally to the clamping device 100.

A handle 019 is attached at the distal holding segment 017. A medical instrument, for example, can be fastened at the free end of the handle 019 or of the holding system 200. For this purpose, the distal end of the handle 019 has a coupling unit 170. This coupling unit 170 can preferably be configured as a quick-coupling unit such as the known KSLOCK interface. Various medical instruments, such as micro-scissors, forceps, tweezers, punches or the like, can be attached to an autoclavable quick-coupling unit 170 of this kind. Moreover, the holding device 20, releasable via the coupling device 300, can be sterilized. For an operation, the clamping device 100 and other non-sterilizable elements are to be covered with a suitable drape. With a transparent drape, light displays or other important switching elements can still be seen or controlled by the operating person.

Besides the connection to the wrist joint 018, which is preferably configured as a ball joint, and the quick-coupling unit 170, the handle 019 has an actuation element 169. The drive unit 160 of the clamping device 100 can be activated by the distal actuation element 169. The control signal for activation or actuation of the illustrated spindle 110 can be conveyed via the cable 168 to the drive unit 160. The cable 168 is partially guided along the holding segments 017 and 001. Between the proximal holding segment 001 and the distal holding segment 017, the cable 168 is guided with a degree of play, such that the central joint 21 can move freely. To protect the cable, the pivotability of the joint 21 is advantageously limited to 340°.

When the cable 168 is guided to the proximal end of the holding segment 001, it passes into the bolt element 301 as shown in the preceding figures. The guiding of the cable into the bolt element 301 of the coupling device allows the control signals to be routed via the coupling device 300 to the drive unit 160. In the interior, the coupling device 300 has suitable contact elements for ensuring that the signal conveyed via the cable can be forwarded to the drive unit 160. As an alternative to the cabled activation, radio-controlled actuation of the clamping device 100 is also conceivable.

In the example shown, the drive unit 160 for the spindle 101 comprises an electric motor 161 with a gear 162. The drive unit 160 is powered by an accumulator 163, of which the charging state can be displayed. The accumulator 163 is arranged in the accumulator well 164 and is controlled by the accumulator control unit 165. Furthermore, a drive control unit 166 and a switching logic 167 are located in the housing. The spindle 110 can be driven by means of the gear 162 of the electric motor 161.

The pushing elements 002, 118, holding segments 001, 019, 101 and joints 21, 152 of the holding system 200 are designed depending on the forces that are to be passed through and depending on the parts, instruments or end effectors that are to be attached. The maximum reach of the holding system, and at the same time the greatest load, is attained when the arm is extended horizontally. In this position, the holding system according to the invention is intended to attain holding forces of between at least 3 kg and 5 kg. The reaches of the entire holding system are, for example, between 55 cm and 71 cm. For uses in sterile environments, it is necessary to sterilize the holding device 020 and attachment parts. Parts of the holding system 200 not intended for sterilization, such as coupling device 300 and clamping device 100, can be covered with a sterile drape which has a suitable opening for attachment of the sterile holding device 20 to the coupling device 300.

Moreover, the coupling device 300 is designed such that the bolt element 301 can move freely about the main axis, as long as no clamping force or tensile force Fz is transmitted between the coupling parts 301 and 302. In medical uses, this degree of rotational freedom of the coupling device 300 and of the holding system 200 can advantageously allow the operator of the distal instrument a further degree of freedom.

Figure 6:
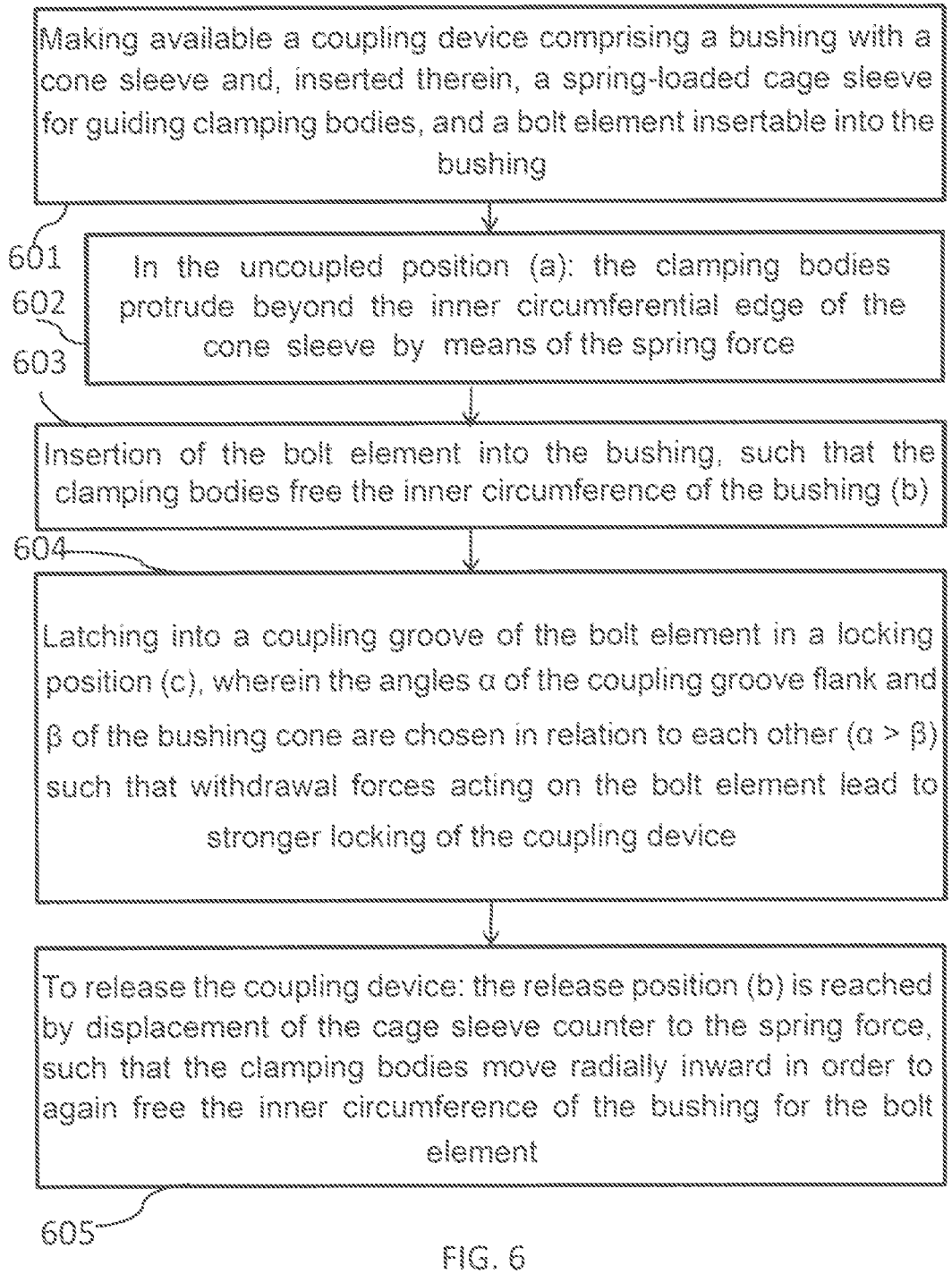
FIG. 6 shows a schematic diagram of a method for the self-securing mechanical connection of two parts of a holding system.

FIG. 6 shows the principal method steps for coupling and releasing a coupling device 300 according to the present invention. The first method step 601 comprises making available a coupling device 300 comprising a bushing 302 with a cone sleeve 321 and, inserted therein, a spring-loaded cage sleeve 329 guiding clamping bodies, and a bolt element 301 insertable into the bushing 302.

The second method step 602 relates to the uncoupled position (a) of the coupling device, in which the clamping bodies protrude beyond the inner circumferential edge of the cone sleeve 321 by means of the spring force.

Method step 603 comprises inserting the bolt element 301 into the bushing 302, such that the clamping bodies 324 free the inner circumference of the bushing 302. The so-called release position (b) of the coupling device is thus obtained.

The self-securing coupling method moreover comprises the method step 604 essential to coupling, wherein the clamping bodies 324 latch into a coupling groove 303 of the bolt element 301 in a locking position (c) and the angles α of the coupling groove flank of the bolt element 301 and β of the bushing cone are chosen in relation to each other such that α is greater than β and withdrawal forces acting on the bolt element 301 thus lead to stronger locking of the coupling device 300.

The chosen angles α and β have the advantageous effect that, as soon as an operating force acts counter to the insertion direction, the clamping bodies 324 are pressed into the clamping groove 303 or into the locking position (c). This prevents a situation where withdrawal forces generate an inadvertent release of the coupling device 300.

In order to release the coupling device 300, the release position (b) can again be reached in the following method step 605:

Displacement of the cage sleeve 329 counter to the spring force, such that the clamping bodies 324 move radially inward in order to again free the inner circumference of the bushing for the bolt element 301. For this purpose, an actuation element 325 in the form of a displaceable ring is advantageously used, which can be operated using one hand.

Figure 7:
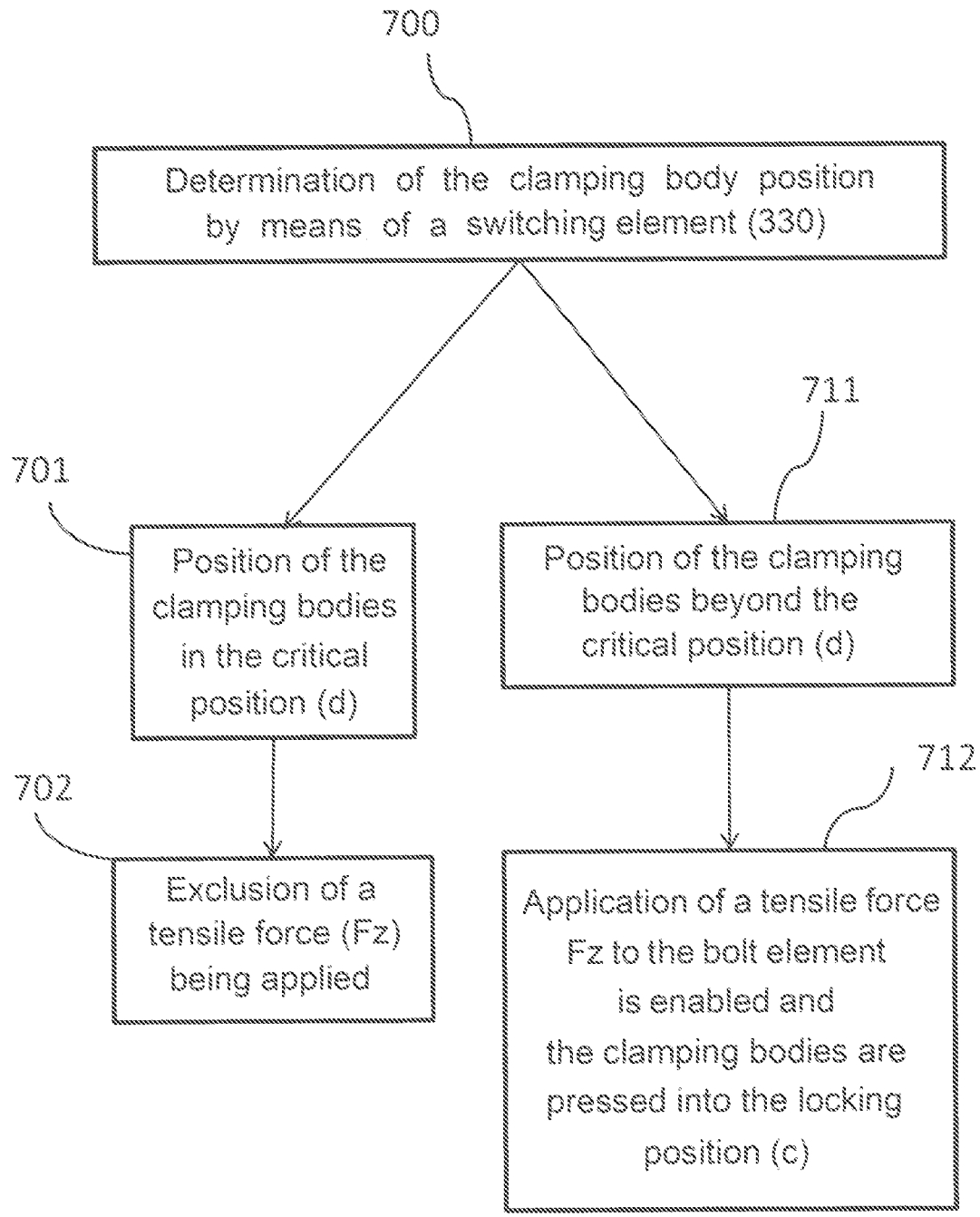
FIG. 7 shows a further schematic diagram of a method for determining a clamping body position and for enabling application of tensile force to a bolt element in accordance with the clamping body position.

FIG. 7 shows a method 700 for the coupling device 300 according to the invention, wherein the clamping body position is determined by means of a switching element 330 and associated switching mechanism.

When, in method step 701, the determined position of the clamping bodies 324 is the critical position (d) in which the clamping bodies 324 are located in the region between the inner circumferential edge 323 of the cone sleeve 321 and the outer circumferential edge of the coupling groove 303, method step 702 follows. Method step 702 excludes the possibility of tensile force (Fz) being applied to the bolt element 301. In this way, it is possible to prevent the coupling device from inadvertently coming loose.

By contrast, when a position of the clamping bodies 324 beyond the critical position (d) is determined in method step 711, the application of a load is enabled in method step 712. Even when the clamping bodies 324 are not completely latched but are located beyond the critical position (d), the clamping bodies 324 are pressed into the locking position (c) in method step 712. This self-securing coupling method is based principally on the abovementioned chosen angle difference γ between the front inclined coupling groove flank 304 of the bolt element 302 and the inclination of the cone inner face 322 of the bushing cone sleeve 321.

By making available a plurality of switching elements 300 and associated limit switches 324, a redundant control possibility or monitoring of the clamping body positions is made available. In this way, it is possible to reliably determine whether a bolt element 301 has been inserted into the coupling bushing 302 sufficiently so as not to be able to be withdrawn under tensile load. Particularly if the clamping bodies 324 are located in a so-called critical position in which the bolt element can be positioned under load either in the release position (b) or in a locking position (c), the risk of the bolt 301 being inadvertently released can be minimized with the aid of the precise and redundant determination of the clamping body position.

The invention relates to a coupling device 300 and coupling method for the self-securing mechanical connection of two parts of a holding system for medical instruments, comprising a bolt element 301 insertable into a bushing 302; wherein the bushing 302 has a main body and, connected fixedly to the latter, a cone sleeve which tapers conically at its free end, wherein a cage sleeve acted upon by a spring and guiding clamping bodies is inserted axially movably into the cone sleeve and can be moved between an uncoupled position a, a release position b and a locking position c. The clamping bodies 324 in the locking position c can be latched into a coupling groove 303 of the bolt element 301 by means of the spring force. The inclined coupling groove flank 304, at the front in the insertion direction, of the bolt element 301 encloses an angle α with the longitudinal axis of the bolt element 301, and the cone inner face 322 of the cone sleeve 321 encloses an angle β with the central sleeve axis. The coupling device 300 is characterized in that, for self-securing connection, the angle α is greater than the angle β such that clamping bodies partially or completely latched into the coupling groove can be pressed into the locking position c counter to the insertion direction by application of a tensile force Fz to the bolt element.

The invention claimed is:

1. A coupling device for a self-securing mechanical connection of two parts of a holding system for medical instruments, comprising:
   a bolt element insertable into a bushing;
   wherein the bushing has a main body and a cone sleeve connected fixedly to the main body, wherein a free end of the cone sleeve tapers conically;
   wherein a cage sleeve acted upon by a spring and guiding clamping bodies is inserted axially movably into the cone sleeve; wherein
   (a) the clamping bodies, in an uncoupled position, protrude radially beyond an inner circumferential edge of the cone sleeve by means of a spring force of the spring acting on the cage sleeve;
   (b) the clamping bodies, in a release position, are movable radially inward by displacement of the cage sleeve counter to the spring force along a cone inner face of the cone sleeve, in order to free an inner circumference of the bushing for the bolt element; and
   (c) the clamping bodies, in a locking position, are latched into a coupling groove of the bolt element by means of the spring force;
   wherein the bolt element has a front inclined coupling groove flank, at a front in an insertion direction, wherein the front inclined coupling groove flank encloses an angle ($\alpha$) with a longitudinal axis of the bolt element;
   wherein the cone inner face of the cone sleeve encloses an angle ($\beta$) with a central sleeve axis;
   wherein, for self-securing connection, the angle ($\alpha$) is greater than the angle ($\beta$) such that the clamping bodies partially or completely latched into the coupling groove are pressed into the locking position counter to the insertion direction by application of a tensile force (Fz) to the bolt element;
   wherein the coupling device further comprises at least one switching element in order to determine a clamping body position and to exclude a critical position of the clamping bodies in which, after application of the tensile force (Fz) to the bolt element, the clamping bodies are adapted to be pressed either into the release position or the locking position;
   wherein the critical position of the clamping bodies is located in a region between the inner circumferential edge of the cone sleeve and an outer circumferential edge of the coupling groove; and
   wherein, by means of the switching element, the application of tensile force (Fz) to the bolt element is adapted to be enabled only when the clamping body position that has been determined is a position beyond the critical position, wherein the clamping bodies are positioned partially or completely latched on the bolt element in the locking position.

2. The coupling device according to claim 1, wherein a difference ($\gamma$) of the angles ($\alpha$, $\beta$) is between 1° and 15°.

3. The coupling device according to claim 2, wherein the angle ($\alpha$) of the front inclined coupling groove flank of the bolt element encloses an angle of between 5° and 60°, and the angle ($\beta$) of the cone inner face encloses an angle of between 10° and 55°.

4. The coupling device according to claim 2, further comprising an actuation element connected to the cage sleeve, wherein the cage sleeve guiding the clamping bodies is movable, by means of the actuation element, to the release position counter to the spring force of the spring, which is arranged between the cone sleeve and the actuation element.

5. The coupling device according to claim 1, wherein the angle ($\alpha$) of the front inclined coupling groove flank of the bolt element encloses an angle of between 5° and 60°, and the angle ($\beta$) of the cone inner face encloses an angle of between 10° and 55°.

6. The coupling device according to claim 1, wherein the main body has a plurality of guide gaps in each of which a switching element designed as a switching pin is axially movable by means of the cage sleeve, wherein each switching pin has a switching cam at a free end in order to actuate a limit switch for enabling the tensile force (Fz) according to the position of the clamping bodies.

7. The coupling device according to claim 6, wherein the limit switches are surrounded by a transparent cover element which has at least one lighting element in order to provide light in accordance with an actuation of the limit switches.

8. The coupling device according to claim 1, further comprising an actuation element connected to the cage sleeve, wherein the cage sleeve guiding the clamping bodies is movable, by means of the actuation element, to the release position counter to the spring force of the spring, which is arranged between the cone sleeve and the actuation element.

9. The coupling device according to claim 8, wherein the actuation element is designed as an actuation ring, and the spring is designed as a wave washer.

10. The coupling device according to claim 1, further comprising an ejector spring in order to eject the released bolt element in the release position, such that re-engagement of the clamping bodies in the coupling groove is prevented.

11. The coupling device according to claim 1, wherein the bolt element and the bushing are freely rotatable relative to each other.

12. The coupling device according to claim 1, wherein the clamping bodies are designed as balls, barrel rollers or cylinder rollers.

13. The coupling device according to claim 1, wherein at least one contact face for electrically connecting a signal line to at least one contact element of the main body is formed at an end of the bolt element.

14. The coupling device according to claim 13, wherein a plurality of contact faces, and a plurality of contact elements insulated from one another via an insulating sleeve, are provided, and each contact face of the bolt element is electrically connectable to a respective contact element of the main body.

15. A holding system comprising a coupling device according to claim 1,
   wherein a first part of the holding system is a clamping device; and
   wherein a second part of the holding system is a holding device for medical instruments.

16. The holding system according to claim 15,
   wherein the main body of the bushing is designed such that an end of an axially displaceable pushing element of the clamping device is adapted to be arranged protruding into the main body; and
   wherein the bolt element is connectable to a proximal holding segment of the holding device such that a proximal end of a pushing element displaceable in the holding segment and in the bolt element is adapted to be arranged protruding beyond a front side of the bolt element; and
   wherein in the locking position of the coupling device, and by means of the pushing element of the clamping device displaceable via a spindle, the proximal end of the pushing element of the coupled holding device is axially displaceable counter to the insertion direction of the bolt element to permit locking with frictional engagement.

17. A method for a self-securing mechanical connection of two parts of a holding system for medical instruments, comprising the following steps:
providing a coupling device with a bolt element insertable into a bushing, wherein the bushing has a main body and a cone sleeve connected fixedly to the main body, wherein a cage sleeve acted upon by a spring and guiding clamping bodies is used and is movable axially between an uncoupled position, a release position, and a locking position; wherein
(a) in the uncoupled position, the clamping bodies protrude radially beyond an inner circumferential edge of the cone sleeve by means of a spring force of the spring,
(b) in the release position, the clamping bodies are moved radially inward by displacement of the cage sleeve counter to the spring force along a cone inner face of the cone sleeve, in order to free an inner circumference of the bushing for the bolt element; and
(c) in the locking position, the clamping bodies latch into a coupling groove of the bolt element by means of the spring force;
wherein when a tensile force (Fz) is applied to the bolt element, the clamping bodies partially or completely latched into the coupling groove are pressed into the locking position counter to an insertion direction, since an angle ($\alpha$) of a front inclined coupling groove flank of the bolt element is greater than an angle ($\beta$) of the cone inner face of the cone sleeve;
determining a clamping body position by means of a switching element, in order to exclude a critical position of the clamping bodies in which, after application of the tensile force (Fz) to the bolt element, the clamping bodies are adapted to be pressed either into the release position or the locking position;
wherein the critical position of the clamping bodies is located in a region between the inner circumferential edge of the cone sleeve and an outer circumferential edge of the coupling groove; and
enabling application of tensile force (Fz) to the bolt element by means of the switching element when the clamping body position that has been determined is a position beyond the critical position, wherein the clamping bodies are positioned partially or completely latched on the bolt element in the locking position.

* * * * *